(12) United States Patent
Kashani et al.

(10) Patent No.: US 11,801,343 B2
(45) Date of Patent: Oct. 31, 2023

(54) METHODS AND SYSTEMS FOR DELIVERING MATERIAL TO A BODY PART

(71) Applicant: Alcon Inc., Fribourg (CH)

(72) Inventors: Pooria Sharif Kashani, Irvine, CA (US); Omeed Paydar, Irvine, CA (US)

(73) Assignee: Alcon Inc., Fribourg (CH)

( * ) Notice: Subject to any disclaimer, the term of this patent is extended or adjusted under 35 U.S.C. 154(b) by 234 days.

(21) Appl. No.: 16/505,227

(22) Filed: Jul. 8, 2019

(65) Prior Publication Data

US 2020/0016334 A1 Jan. 16, 2020

Related U.S. Application Data

(60) Provisional application No. 62/696,983, filed on Jul. 12, 2018.

(51) Int. Cl.
*A61M 5/168* (2006.01)
*A61M 5/145* (2006.01)
*A61M 5/172* (2006.01)

(52) U.S. Cl.
CPC .... *A61M 5/16877* (2013.01); *A61M 5/14546* (2013.01); *A61M 5/1684* (2013.01); *A61M 5/172* (2013.01); *A61M 2205/0216* (2013.01); *A61M 2205/078* (2013.01); *A61M 2205/3331* (2013.01); *A61M 2205/3584* (2013.01); *A61M 2205/502* (2013.01); *A61M 2210/0612* (2013.01)

(58) Field of Classification Search
CPC .............. A61M 5/172; A61M 5/16877; A61M 5/1684; A61M 2205/078; A61M 2205/3331; A61M 2205/502; A61M 5/1452; A61M 2205/3341; A61M 2205/3334; A61B 2090/064
See application file for complete search history.

(56) References Cited

U.S. PATENT DOCUMENTS

| | | | |
|---|---|---|---|
| 5,019,037 A | 5/1991 | Wang | |
| 5,120,307 A * | 6/1992 | Wang | A61F 9/00736 604/506 |
| 6,290,690 B1 | 9/2001 | Huculak et al. | |
| 8,118,790 B2 | 2/2012 | Dacquay et al. | |
| 2004/0024361 A1 | 2/2004 | Fago | |
| 2005/0059926 A1* | 3/2005 | Sage | A61M 5/16881 700/282 |
| 2005/0228423 A1 | 10/2005 | Khashayar | |
| 2007/0038174 A1 | 2/2007 | Hopkins | |

(Continued)

FOREIGN PATENT DOCUMENTS

| | | |
|---|---|---|
| JP | 2004-507319 A | 3/2004 |
| JP | 2011-101744 A | 5/2011 |

(Continued)

*Primary Examiner* — William R Carpenter
(74) *Attorney, Agent, or Firm* — PATTERSON & SHERIDAN, LLP (57) ABSTRACT

Certain aspects of the present disclosure provide a surgical system comprising a fluid output device capable of connecting to a syringe comprising a material for delivery to a body part through a cannula connected to the syringe and a controller configured to adjust a pressure of the fluid output to enable a controlled delivery of the material within the syringe at a target flow rate.

10 Claims, 5 Drawing Sheets

(56) References Cited

U.S. PATENT DOCUMENTS

| | | |
|---|---|---|
| 2007/0185496 A1* | 8/2007 | Beckman .......... A61B 17/8822 606/93 |
| 2008/0097379 A1 | 4/2008 | Dacquay |
| 2008/0097390 A1 | 4/2008 | Dacquay |
| 2008/0125712 A1 | 5/2008 | Dacquay |
| 2009/0030366 A1 | 1/2009 | Hochman |
| 2009/0062808 A1* | 3/2009 | Wolf, II ............. A61B 17/8822 606/92 |
| 2009/0157040 A1* | 6/2009 | Jacobson .......... A61M 5/16854 702/45 |
| 2009/0177182 A1 | 7/2009 | Hickingbotham |
| 2009/0221986 A1* | 9/2009 | Wang .................. A61M 5/1723 604/503 |
| 2009/0270844 A1 | 10/2009 | Seeley et al. |
| 2009/0292290 A1* | 11/2009 | Truckai .............. A61B 17/8822 606/93 |
| 2010/0030220 A1* | 2/2010 | Truckai .............. A61B 17/8816 606/93 |
| 2010/0274180 A1* | 10/2010 | Donovan ........... A61M 5/1452 604/65 |
| 2011/0295191 A1 | 12/2011 | Injev |
| 2012/0089114 A1 | 4/2012 | Hemond et al. |
| 2016/0081732 A1* | 3/2016 | Baroud ................ A61M 5/142 623/23.62 |
| 2017/0333253 A1 | 11/2017 | Heeren |
| 2019/0254870 A1 | 8/2019 | Hopkins |

FOREIGN PATENT DOCUMENTS

| | | |
|---|---|---|
| WO | 0217825 A3 | 3/2002 |
| WO | WO2013075109 A2 | 5/2013 |
| WO | WO2016127121 A1 | 8/2016 |
| WO | WO2017199135 A1 | 11/2017 |
| WO | WO2018013493 A1 | 1/2018 |

* cited by examiner

METHODS AND SYSTEMS FOR DELIVERING MATERIAL TO A BODY PART

PRIORITY CLAIM

This application claims the benefit of priority of U.S. Provisional Patent Application Ser. No. 62/696,983 titled "Methods and Systems for Delivering Material to a Body Part," filed on Jul. 12, 2018, whose inventors are Pooria Sharif Kashani and Omeed Paydar, which is hereby incorporated by reference in its entirety as though fully and completely set forth herein.

INTRODUCTION

Aspects of the present disclosure generally relate to methods and systems for delivering material to a body part.

During surgical procedures, a surgeon may deliver or inject various types of materials into a certain body part under operation. Different materials, used for different surgeries, may have different properties. Properties of some of these materials may change over time. As an example, some material may be viscous or viscoelastic, meaning the material exhibits both solid like and/or fluid like behavior. In some cases, the viscosity of such a material may, for example, increase with time due to a certain event, such as the exposure of the material to air, a change in temperature, or a mixing of the material with another material. For example, a surgeon may take a viscous material out of a container, mix the material with another material, and load the mixed material into a syringe for delivery to a body part. After the mixed material is loaded into the syringe, the viscosity of the mixed material may increase with time. As the viscosity of the mixed material increases and the mixed material begins to solidify, the surgeon needs to apply more manual pressure to the syringe's plunger to deliver the mixed material.

However, it may be difficult for a surgeon to determine how much additional pressure needs to be exerted on the plunger to deliver the mixed material at a certain target flow rate, when the material's viscosity is changing with time. In addition, after a certain time has passed from when the mixture is prepared, the mixed material solidifies to a point where it becomes exceedingly difficult and cumbersome for the surgeon to apply additional manual pressure to continue the delivery of the material. As a result, the surgeon may be unable to deliver the entire dose of material that is in the syringe and required to be delivered to the body part. Manually delivering the material in an uncontrolled fashion while adjusting (e.g., increasing) the pressure on the syringe's plunger may result in delivering imprecise amounts of the material to the body part.

In addition to viscous material, there is a myriad of other materials with properties that change over time. An uncontrolled and manual delivery of such materials may pose similar issues, as described above. Existing solutions that use surgical systems to automatically deliver material to a patient's body part may not take into account the properties of the material being delivered as well as the change in such properties over time.

BRIEF SUMMARY

The present disclosure relates to methods and systems for delivering material to a body part. Certain embodiments provide a surgical system comprising a fluid output device capable of connecting to a syringe comprising a material for delivery to a body part through a cannula connected to the syringe. In certain embodiments, the surgical system further comprises a controller configured to adjust a pressure of the fluid output to enable a controlled delivery of the material to the body part at a target flow rate.

Certain embodiments provide a method of delivering a material to a body part through a syringe. The method includes receiving an indication to initiate a delivery of the material. The method further includes exerting pressure on a plunger of the syringe to deliver the material to the body part. The method also includes adjusting the pressure on the plunger to enable a controlled delivery of the material at a target flow rate.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Aspects of the present disclosure relate generally to methods and systems for delivering material to a body part. In order to resolve the deficiencies relating to existing solutions, certain embodiments herein describe a surgical system that is configured to deliver material to a body part in a controlled manner and at a target volumetric flow rate ("target flow rate").

Figure 1:
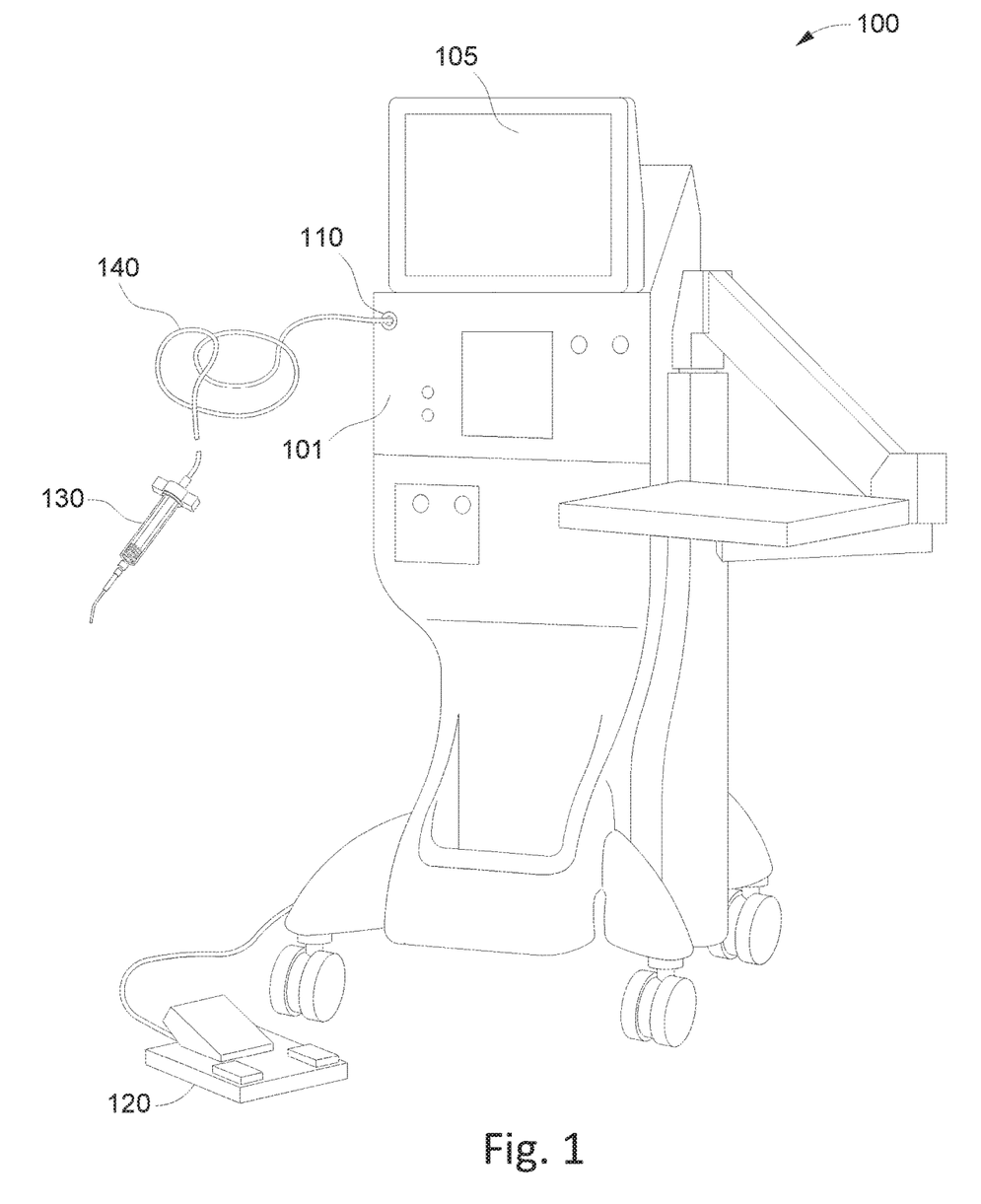
FIG. 1 illustrates an exemplary surgical system for delivery of a material to a body part, in accordance with certain embodiments.

FIG. 1 illustrates an exemplary surgical system 100 that facilitates an operation of syringe 130 to enable a controlled delivery of a material (hereinafter referred to as "material A") within syringe 130 to a body part (e.g., body cavity) of a human or animal. Surgical system 100 comprises a user interface 105, an output device 110, a foot pedal 120, and a control module 101 (e.g., a controller). User interface 105 is used by a user (e.g., surgeon) to provide input to or select a functionality of surgical system 100. Foot pedal 120 is an initiation element used to initiate a functionality, such as the delivery of material A, and provide input (e.g., target flow rate) to control module 101. As shown, surgical system 100 is connected to syringe 130 for use by a surgeon to deliver material A. Surgical system 100 and syringe 130 are connected together via connector 140. At one end, connector 140 is connected to output device 110 of surgical system 100 while, at the other end, connector 140 connects to syringe 130.

In the example of FIG. 1, surgical system 100 enables a controlled delivery of a material within syringe 130 using a fluid dispensed by output device 110. Output device 110 is a fluid output device that outputs a fluid, such as a liquid (e.g., water), air, or gas, into connector 140, which is an elastomer fluid conduit or air tube. Once dispensed by output device 110, the fluid travels to the other end of connector 140, which is coupled to an adaptor that is attached to syringe 130. The adaptor relays the pressure of the fluid onto a plunger of syringe 130, causing material A to be delivered.

As described above, material A may have certain physical properties that change over time. As an example, material A may be a highly viscous material whose viscosity increases with time after it is loaded into a syringe. As another example, material A may have a viscosity that decreases as pressure is applied or material A starts to shear (e.g., in flow). In order to enable a controlled delivery of material A at a target or desired flow rate, control module 101 is configured to adjust the pressure with which a fluid is dispensed from output device 110 based on the properties of material A and/or information from sensors provided to the control module 101. The adjustment in the fluid pressure causes an adjustment of the pressure placed on the plunger of syringe 130, thereby, enabling a controlled delivery of material A. A flow rate refers to a volume of material that passes per unit of time.

In some embodiments, control module 101 stores or is pre-configured with a profile of material A that includes information about or based on the material's physical properties. Alternatively, information about the material's properties may be provided to control module 101 as an input through user interface 105. In some embodiments, the information may include a properties function (e.g., viscosity function) that shows the change in one or more properties of material A over time. Such a function can be used by control module 101 to determine the amount of pressure that must be applied on the plunger to deliver material A at a target flow rate at any point in time.

In some embodiments, the target flow rate may be altered or adjusted during the delivery of material A. For example, a user may wish to control and adjust the flow rate during the delivery using foot pedal 120. In such an example, the amount of pressure the surgeon exerts on foot pedal 120 may linearly and proportionally correspond to the change in the target flow rate. For instance, control module 101 may be configured with a flow rate range of 0 cc/min to X cc/min. In that example, pressing foot pedal 120 half way sends an indication to control module 101 that the user requires a flow rate of X/2. Similarly, pressing foot pedal 120 all the way sends an indication to control module 101 that the user requires a flow rate of X. Once an indication of the target or required flow rate is received by control module 101, control module 101 uses information about material A's properties (e.g., material A's properties function) to determine a corresponding pressure that needs to be applied on the plunger for achieving the target flow rate at that point in time. Consider another embodiment where pressing the pedal may induce a constant ramp from 0 to X over a prescribed period of time.

In some other embodiments, a user may wish to keep the flow rate constant throughout the delivery of material A. In certain aspects, the constant target flow rate may be included in material A's profile. In certain aspects, the user may provide the constant target flow rate as an input into control module 101 (e.g., through user interface 105 or foot pedal 120) and indicate to control module 101 that the flow rate must remain constant at the target rate. Based on the constant flow rate, control module 101 may be configured to determine or calculate a pressure function for material A using the information included in material A's profile or provided through user interface 105. In some embodiments, the profile of material A includes the pressure function of material A.

A pressure function can be used by control module 101 to determine the amount of pressure that must be applied on the plunger to deliver material A at the constant target flow rate at any point in time. Accordingly, when delivering material A, control module 101 dynamically adjusts the pressure that is exerted on the plunger based on the determined pressure function of material A in order to maintain the flow rate constant at the target rate.

As an example, material A's profile may include information about the viscosity of material A. The information may, more specifically, include a viscosity function (e.g., $\mu(t)$) indicating the change in the viscosity of material A over time. In embodiments where the surgeon changes the flow rate throughout the surgery, control module 101 dynamically adjusts the pressure based on the target flow rate and the viscosity function of material A. For example, the flow rate of material A is directly proportional to material A's pressure function with respect to time and indirectly proportional to material A's viscosity function with respect to time ($\mu(0)$). In other words, volumetric flow rate $(Q)=C*P/\mu(t)$, where C is a coefficient constant and P is the pressure applied on the plunger. Accordingly, using a target flow rate as well as the viscosity function of material A, control module 101 is able to determine the amount of pressure that must be used to achieve the target flow rate.

As an example, at t1, the surgeon may press foot pedal 120 half way through, which indicates to control module 101 that the surgeon is requesting a flow rate of X/2 (e.g., assuming a flow rate range of 0 cc/min to X cc/min). Using the target flow rate and the viscosity function of material A, control module 101 then determines the pressure to apply to the plunger at t1. At t2, the surgeon may press foot pedal 120 all the way through, which indicates to control module 101 that the surgeon is requesting a flow rate of X (e.g., assuming flow rate range of 0 cc/min to X cc/min). Using the target flow rate and the viscosity function of material A, control module 101 then determines the pressure to apply to the plunger at t2.

In embodiments where the flow rate is required to be constant throughout the surgery, control module automatically and periodically determines the right amount of pressure to apply on the plunger using the viscosity function and the constant target flow rate. In another example, control module 101 determines a pressure function for material A that can be used to determine the right amount of pressure to apply at any point in time to achieve the constant target flow rate.

In some embodiments, the profile of material A comprises a delivery time threshold. The time threshold may indicate to control module 101 when to terminate the delivery of material A. For example, a time threshold may be t minutes, in which case, control module 101 may terminate the delivery of material A after t minutes by reducing the pressure that is exerted on syringe 130's plunger to zero (e.g., or lower as described below). In embodiments where the profile of material A comprises viscosity information, the time threshold may be based on the viscosity of material A. For example, after t minutes, material A's viscosity may reach a point at which delivering material A to the body part would not be practical or beneficial. At that point, for example, material A may have solidified to a point where the material may not be able to function as intended in the body part or precise delivery may be impaired.

In some embodiments, the profile of material A may comprise a pressure threshold. The pressure threshold indicates to control module 101 when (i.e., at what pressure) to terminate the delivery of material A. As an example, the profile of material A may indicate a pressure threshold of $P_{Th}$ PSI (pressure per square inch). When reaching $P_{Th}$ PSI during the delivery, control module 101 may be programmed to terminate the delivery based on the pressure threshold by immediately reducing the fluid pressure to zero or lower.

In embodiments where the profile of material A comprises viscosity information, the pressure threshold may be based on the viscosity of material A. For example, a certain pressure value on material A's pressure function may correspond to a certain viscosity value on material A's viscosity function. As described above, after material A's viscosity reaches a certain viscosity threshold, delivering the material may not be beneficial. In such an example, the pressure threshold may correspond to the viscosity threshold.

In embodiments where the profile of material A comprises viscosity information, control module 101 may be configured to terminate the delivery of material A once material A's viscosity reaches a certain threshold. For example, based on the viscosity function ($\mu(t)$) included in material A's profile, control module 101 may determine the state of material A's viscosity at any time (t) during the delivery, where (t) refers to the amount of time that has passed since the delivery of material A started (e.g., delivery time). In some embodiments, the viscosity threshold may also be provided to control module 101 as an input through user interface 105.

In some embodiments, surgical system 100 is configured to determine when a certain volume of material A has been delivered based on a real-time analysis of a delivery time of material A and the constant flow rate. For example, control module 101 may start a timer when initiating the delivery of material A at time (Tx). The time indicated by the timer indicates the delivery time of material A. In embodiments where the flow rate is constant throughout the delivery, multiplying the delivery time by the constant flow rate, provides the volume that has been delivered to the body part since Tx. In embodiments where the flow rate varies throughout the delivery, the total volume delivered at any point may equal a mathematical integral of the flow rate function at that point in time.

In some embodiments, control module 101 is configured to terminate the delivery of material A when a certain volume of material A has been delivered. As a result, control module 101 may periodically calculate the total delivered volume and terminate the delivery once the threshold delivery is reached. In some embodiments, the volume threshold may be provided as an input into control module 101 through user interface 105. In some embodiments, the volume threshold input may be included in the profile of the corresponding material.

In some embodiments, when control module 101 terminates the delivery or the delivery is temporarily paused (e.g., no pressure is applied on the foot pedal), control module 101 may instantly reduce the pressure to a small negative pressure (e.g., −1, or −2 or −5 Millimeter Mercury). This ensures that residual material around the tip of the cannula is pulled back into the cannula so that the tip of the cannula stays clean and residual material does not contaminate other areas around where the material is applied in the body part as the surgeon moves the cannula in and out of body part.

In addition to material A, in some embodiments, surgical system 100 is configured with the profile of other materials. For example, surgical system 100 may be regularly utilized for delivering three types of materials, materials A, B, and C, during surgery. In such an example, a surgeon may select one of materials A, B, or C, that is required to be delivered during an ongoing surgery using user interface 105. Each of materials A, B, and C may have a different profile with different properties that result in a different pressure function and thresholds (e.g., pressure, volume, and time threshold), etc.

FIG. 1 shows one embodiment of a surgical system that facilitates an operation of a syringe. However, other embodiments of a surgical system may also be used.

For example, although surgical system 100 shown in FIG. 1 includes both an output device (e.g., output device 110) and a control module (e.g., control module 101), in some other embodiments, surgical system 100 may comprise a number of separate but connected components, including an output device as well as a separate device comprising a control module. In such embodiments, the output device connects to syringe 130 through connector 140 and receives instructions from the control module device indicating the pressure that should be used for the delivery of the material.

In addition, although output device 110 of FIG. 1 is a fluid device, in some embodiments, output device 110 may be an electrical signal output device that provides electrical signals to an electro-mechanical device for physically moving the plunger. Output device 110 may provide power and electrical signals to the electro-mechanical device for adjusting the pressure on the plunger. The signals, in such embodiments, indicate the pressure or amount of force that needs to be exerted on the plunger. Also, in such embodiments, connector 140 may be an electrical cord for carrying electrical signals from output device 110 to the electro-mechanical device. In some embodiments, the electro-mechanical device may be an actuator or a stepper motor that directly controls the movement of the plunger.

In addition, in some embodiments, instead of or in addition to configuring surgical system 100 to perform pressure adjustment based on the profile of the material being delivered, a flow sensor coupled to syringe 130 is configured to periodically send the real-time flow rate of the material being delivered to surgical system 100. Based on the real-time flow rate, surgical system 100 adjusts the pressure to achieve a target flow rate. For example, the surgeon may provide a constant target flow rate to surgical system 100 as an input. Surgical system 100 then starts delivering the material using a certain starting pressure. As the material is delivered, surgical system 100 periodically (e.g., every millisecond, every second, etc.) receives the real time flow rate of the material from the flow sensor, based on which surgical system 100 then keeps adjusting the pressure on the plunger to achieve and maintain the desired flow rate. In some embodiments, the flow sensor calculates a flow rate by determining the displacement or movement of the plunger over a certain period of time (e.g., every millisecond, every second, etc.). The displacement of the plunger corresponds to the volume or amount of material dispensed.

In some embodiments, instead of a flow sensor, a displacement sensor is used. The displacement sensor calculates the displacement of the plunger and periodically sends the displacement information to surgical system 100. Using that information, in some embodiments, surgical system 100 calculates a flow rate based on the volume of the material that has been dispensed over a certain period of time. In such embodiments, surgical system 100 keeps track of time by starting a time after the delivery of the material is initiated. Using the periodically calculated flow rate, the surgical system is able to adjust the pressure on the plunger and maintain a desired flow rate.

In some embodiments, in addition to or instead of coupling a sensor (e.g., flow sensor, displacement sensors, etc.) to syringe 130, a sensor may be used as a part of surgical system 100. For example, a flow sensor may be used to calculate a flow rate of the fluid (e.g., water) dispensed from output device 110 by determining the volume of the fluid dispensed over a certain period of time. In such an example, the flow rate of the fluid dispensed from output device 110 may be the same as the flow rate of the material being delivered over the same period of time. In another example, a displacement sensor may be used as part of surgical system 100 to calculate a displacement of the plunger by determining the displacement of the fluid that is dispensed by output device 110.

Figure 2:
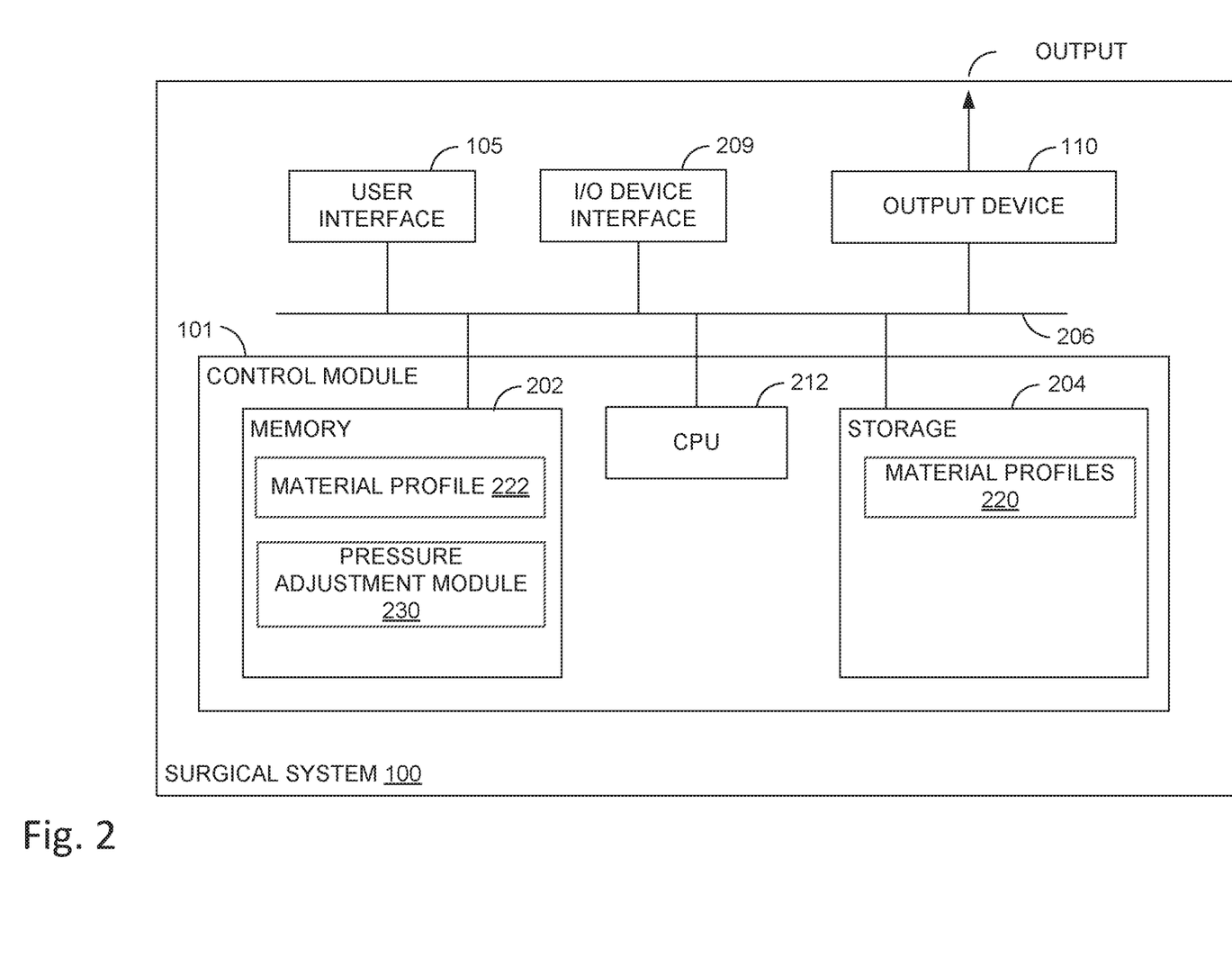
FIG. 2 illustrates exemplary components of the surgical system of FIG. 1, in accordance with certain embodiments.

FIG. 2 illustrates an exemplary diagram showing how the various components of the surgical system 100 of FIG. 1 communicate and operate together. As shown, surgical system 100 includes, without limitation, control module 101, user interface display 105, an interconnect 206, output device 110, and at least one I/O (input/output) device interface 209, which may allow for the connection of various I/O devices (e.g., keyboards, displays, mouse devices, pen input, etc.) to surgical system 100.

Control module 101 (e.g., a controller) may include a central processing unit (CPU) 212, a memory 202, and storage 204. CPU 212 may retrieve and execute programming instructions stored in the memory 202. Similarly, CPU 212 may retrieve and store application data residing in memory 202. Interconnect 206 transmits programming instructions and application data, among CPU 212, I/O device interface 209, user interface 105, memory 202, storage 204, output device 110, etc. CPU 212 can represent a single CPU, multiple CPUs, a single CPU having multiple processing cores, and the like. Additionally, memory 202 represents random access memory. Furthermore, the storage 204 may be a disk drive. Although shown as a single unit, storage 204 may be a combination of fixed or removable storage devices, such as fixed disc drives, removable memory cards or optical storage, network attached storage (NAS), or a storage area-network (SAN).

As shown, storage 204 includes material profiles 220 of various materials (e.g., material profiles A, B, C, etc.) that may be delivered by a surgeon using surgical system 100. Memory 202 includes a pressure adjustment module 230 for adjusting the pressure on a syringe's plunger during the delivery of a material, as described in the embodiments herein. In addition, memory includes a material profile 222 of a material (e.g., material A) being delivered during an operation. For example, once the material is selected for delivery, its profile 222 is retrieved from storage 204 and executed in memory 202. In such an example, pressure adjustment module 230 comprises executable instructions for adjusting the pressure on the plunger based on material profile 222 of the material and the target flow rate, according to the embodiments described herein. In another example, pressure adjustment module 230 comprises executable instructions for adjusting the pressure on the plunger based on information received from a sensor as well as the target flow rate, according to the embodiments described herein.

As shown, surgical system 100 also includes output device 110. As described above, in some embodiments, surgical system 100 exerts force on a syringe's plunger by dispensing a fluid from output device 110. In one example, output device 110 may be a pneumatic output device that dispenses air or gas. In another example, output device 110 may be a hydraulic output device that dispenses liquids, such as water. In some other embodiments, surgical system 100 provides electricity and signals to an electro-mechanical device of the syringe using output device 110. In such embodiments, pressure is exerted on the plunger by the electro-mechanical device using power provided by output device 110.

Figure 3:
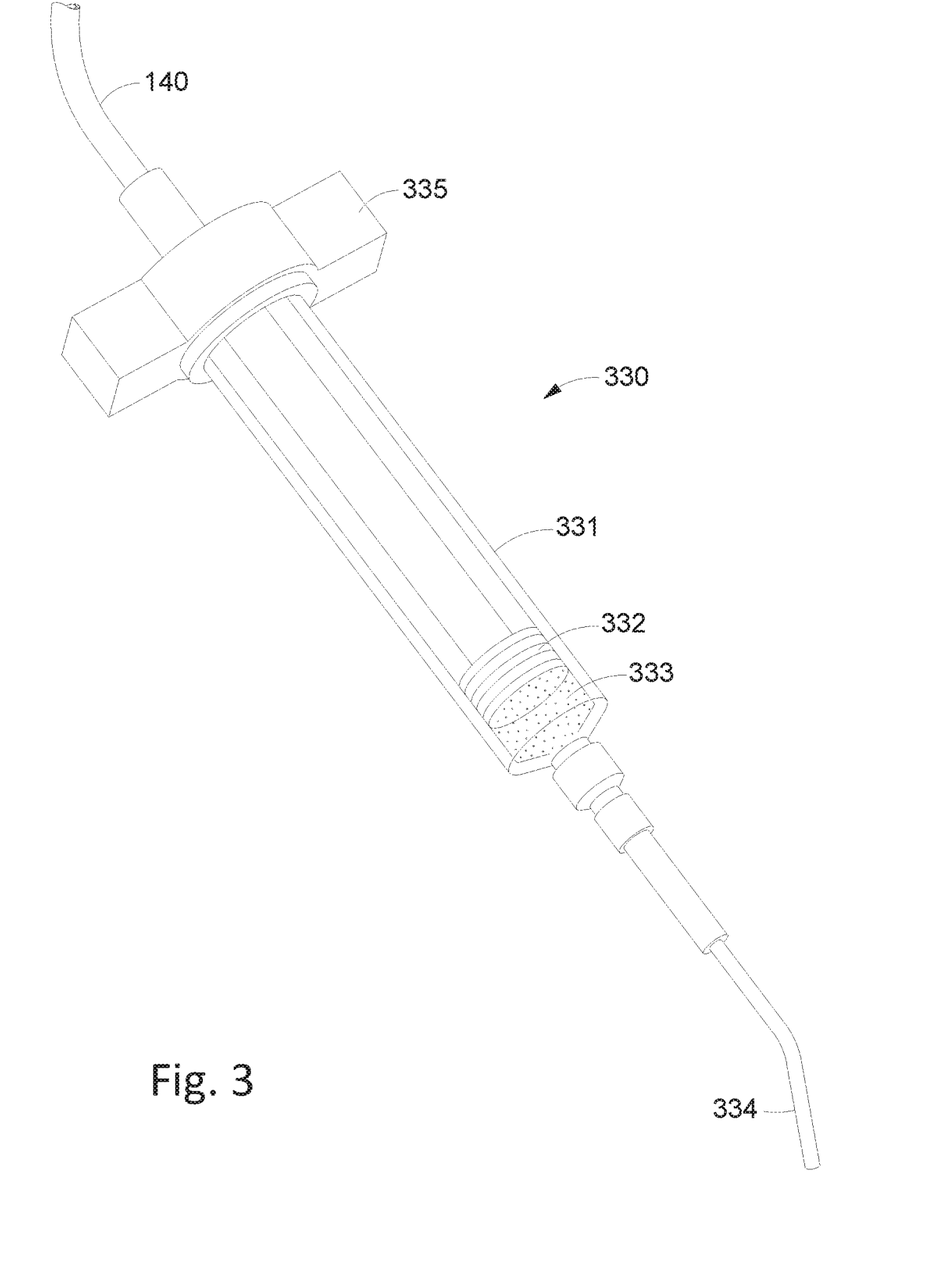
FIG. 3 illustrates an exemplary syringe comprising at least a barrel and a cannula, in accordance with certain embodiments.

FIG. 3 illustrates an exemplary syringe 330 comprising at least a barrel 331 and a cannula 334. Barrel 331 includes a plunger 332 that pushes material 333 out of cannula 334 for delivery. Adaptor 335, as described above, is capable of receiving input from connector 140 and translating that input into a certain amount of pressure on plunger 332. In some embodiments, the input provided by connector 140, as described above, may be pressure associated with the fluid that is dispensed from the output device on the surgical system. In some other embodiments, the input to adaptor 335 may comprise electrical signals to indicate a certain desired pressure. In such embodiments, syringe 330 (e.g., as part of adaptor 335) may comprise an electro-mechanical device that uses the power from connector 140 to exert force on plunger 332.

In some embodiments, as described above, a flow sensor or a displacement sensor is coupled to or formed as a part of syringe 330. In some embodiments, the sensor may communicate with the surgical system wirelessly. For example, the sensor and the surgical system may communicate using Bluetooth or near field communications technologies. In some other embodiments, the sensor and the surgical system may be wired together and communicate using a cord that connects them.

Figure 4:
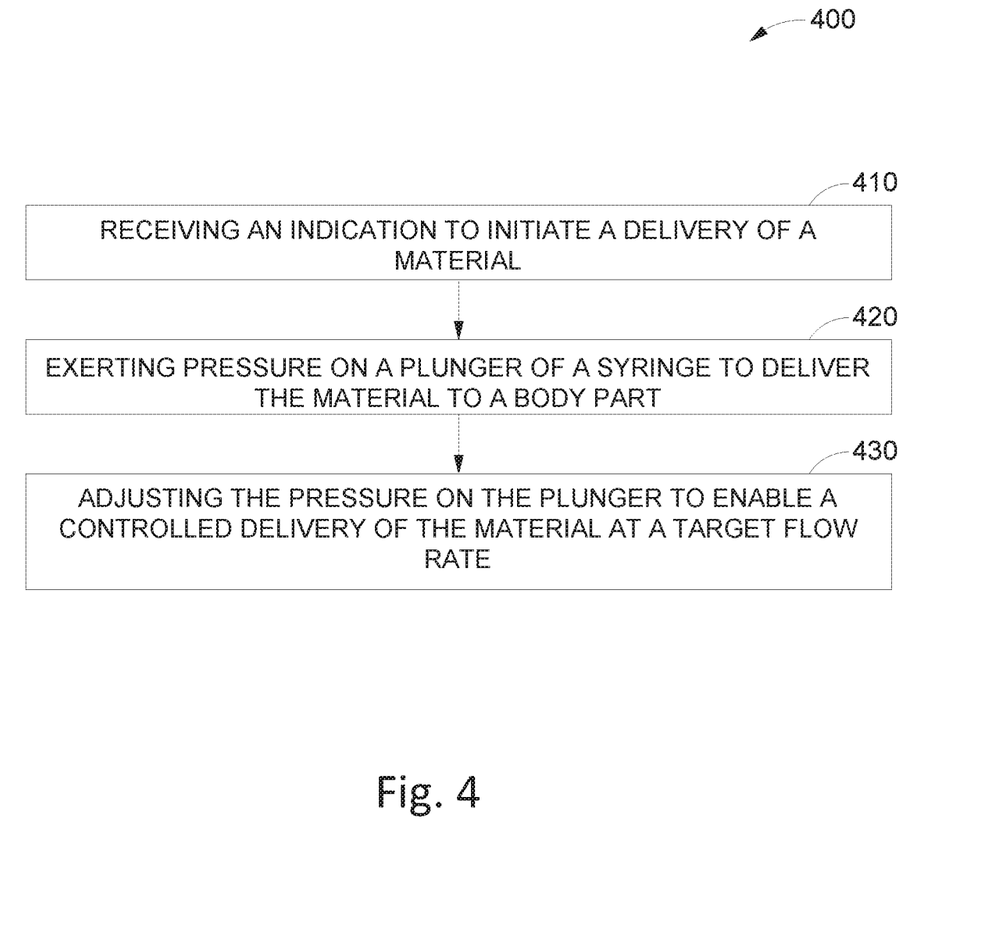
FIG. 4 illustrates example operations for delivering a material to a body part through a syringe, in accordance with certain embodiments.

FIG. 4 illustrates an example method 400 for delivering a material to a body part through a syringe. In some embodiments, method 400 may be performed by a surgical system (e.g., surgical system 100).

At 410, an indication is received by a surgical system to initiate the delivery of the material. For example, a surgeon loads material A into a syringe (e.g., syringe 330) and places the syringe into the body part. The surgeon then uses a delivery initiation element of the surgical system to initiate the delivery. The delivery initiation element is, in some embodiments, the surgical system's foot pedal (e.g. foot pedal 120). In such embodiments, the indication is received from the foot pedal by the surgical system. In response, the surgical system initiates the delivery. In some other embodiments, the delivery initiation element may be the user interface (e.g., user interface 105) or some other input mechanism of the surgical system. In such embodiments, the surgeon may click a button (e.g., user interface element) on the surgical system that initiates the delivery of the material. In some embodiments, a number of different buttons may be used for initiating the delivery of different material. For example, one button may be clicked to initiate the delivery of material A and another may be clicked to initiate the delivery of material B.

As described above, in some embodiments, the surgical system is configured with a profile of material A in order to deliver the material at a target flow rate. For example, when an indication is received by the surgical system to initiate the delivery of material A, the surgical system dynamically uses information in the profile of material A (e.g., properties function) to determine the correct amount of pressure for use to deliver the material at a target flow rate. As described above, in some aspects, the surgical system may be directed to maintain the flow rate constant at a target rate. In such aspects, the surgical system adjusts the pressure to achieve the constant flow rate using information in material A's profile. In some other aspects, the target flow rate may vary throughout the delivery. In such aspects, the surgical system dynamically adjusts the pressure based on the varying flow rate that is received as an input through the delivery initiation element (e.g., foot pedal).

In some embodiments, the surgical system is not pre-configured with a profile of the material that is planned for delivery. In such embodiments, a user enters information about the material or its properties into surgical system 100. The surgical system is then configured to adjust the pressure to deliver the material at a target flow rate based on the inputted information.

In one example described above, material A's profile indicates a viscosity function, based on which surgical system can adjust the pressure for the delivery of material A at the target flow rate at any point in time. In such an example, when the surgical system receives an indication to deliver material A, it may determine or assume that, at that certain point in time (T1), the viscosity of material A is $\mu 0$. However, T1 may correspond to the time when an indication to deliver material A is received by the surgical system and not when, for example, material A begins to solidify in response to an event (e.g., mixing other materials to produce material A, exposing material A to air, etc.).

More specifically, in one example, a surgeon may produce material A at T0 by mixing two other materials together. The surgeon then loads the material A into the syringe and places the syringe into the body part for delivering material A. Subsequently, the surgeon uses the delivery initiation element of the surgical system to initiate the delivery at T1. T1–T0 corresponds to a duration between the time when the surgeon, for example, produces material A as a mixture and the time when the surgeon uses the delivery initiation element to initiate delivery. During this time, the material may have started to become more viscous. For example, at T1, material A may have a viscosity of $\mu 1$ and not $\mu 0$. If the surgical system is not configured to take into account this lag time, the surgical system may use an incorrect amount of pressure for delivering the material. As a result, in some embodiments, the surgical system receives the amount of time (T1–T0) that has passed since the event (e.g., mixing of materials to produce material A, exposing material A to air, etc.), in order to enable the surgical system to determine the correct state of material A (e.g., correct viscosity (e.g., $\mu 1$)) using the properties function (e.g., viscosity function) of material A. This allows the surgical system to accurately determine the pressure throughout the delivery to achieve the target flow rate. In some embodiments, instead of receiving the lag time as an input, the surgical system may be configured or calibrated with a certain fixed lag time.

At 420, pressure is exerted on a plunger of a syringe to deliver the material to the body part. As described above, a number of mechanisms may be used to exert pressure on the plunger of the syringe. For example, in some embodiments, the surgical system may dispense a fluid (e.g., air) from an output device (e.g., output device 110) into a connector (e.g., connector 140) that connects to an adaptor (e.g., adaptor 335) coupled to the syringe. In such embodiments, the pressure of the fluid that is dispensed from the surgical system exerts force on the syringe's plunger. In some other embodiments, the surgical system may provide power and signals through a connector, e.g., electrical cord, to the adaptor to cause a device (e.g., electro-mechanical, mechanical, etc.) to move the plunger.

At 430, the pressure on the plunger is adjusted to enable a controlled delivery of the material at a target rate. As described above, in some embodiments, the surgical system is configured to adjust the pressure on the plunger based on the profile of the material being delivered. In some other embodiments, the surgical system is configured to adjust the pressure based on information (e.g., a real-time flow rate, real-time information about the displacement of the syringe's plunger) received from a flow sensor coupled to the syringe. As described in relation to FIG. 1, the surgical system may be configured to automatically terminate the delivery of the material (i.e., terminate the exerting of pressure on the plunger) upon determining that a certain event has occurred. For example, the surgical system may auto-terminate the delivery if the pressure on the plunger reaches a certain threshold value. In another example, the delivery may be terminated when the delivery time reaches a certain time threshold. In yet another example, the surgical system may terminate the delivery if a certain volume of material has been delivered.

Note that method 400 may be applicable to any type of surgery on any body part. For example, the embodiments described herein are applicable to eye-related surgeries that include an intraocular injection of viscoelastic and phase changing materials into a patient's eye.

Figure 5:
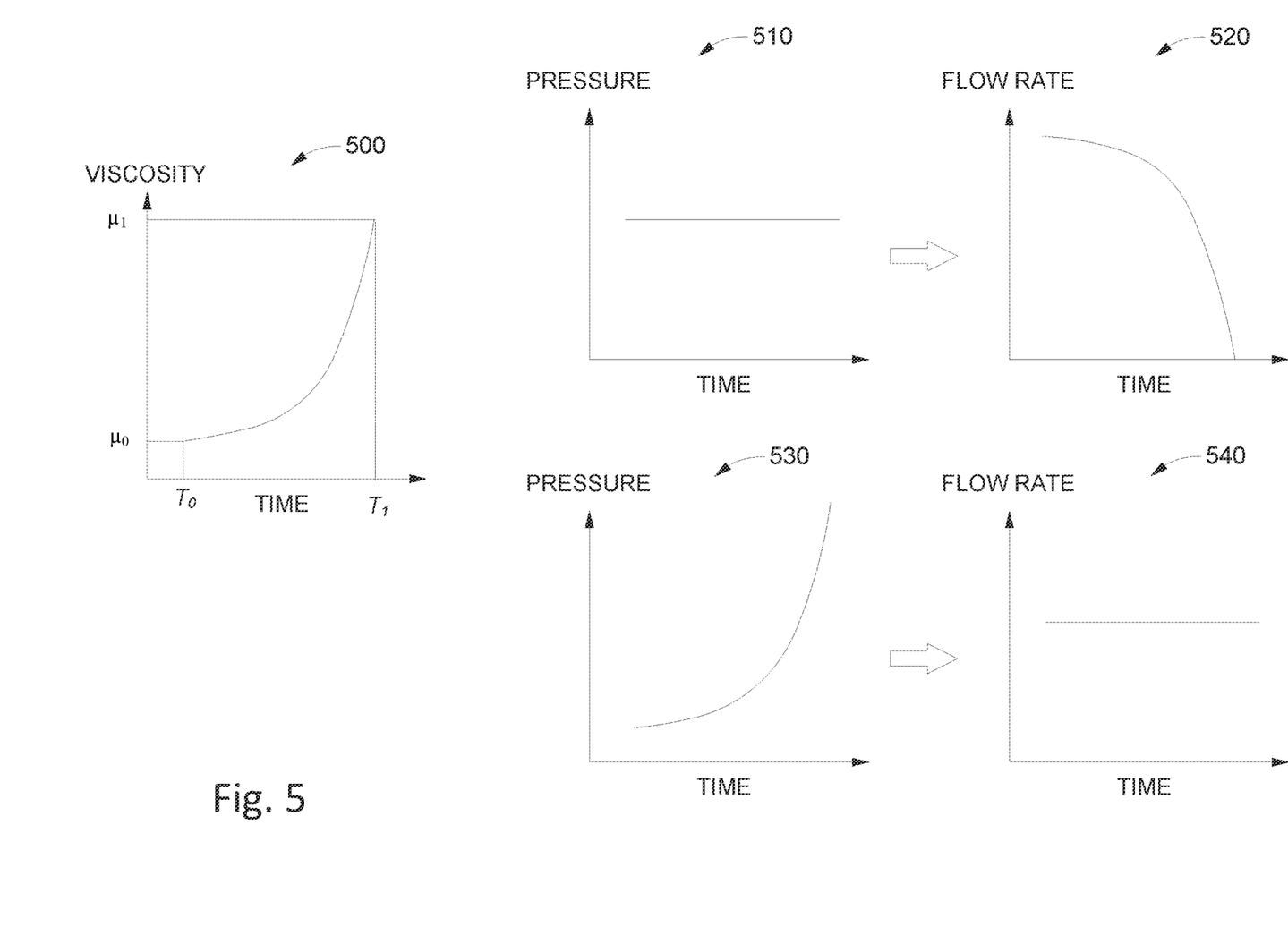
FIG. 5 illustrates example graphs corresponding to a viscous material, in accordance with certain embodiments.

FIG. 5 illustrates a number of exemplary graphs corresponding to a viscoelastic and phase changing material. Graph 500 illustrates the change in the viscosity of the material in relation to time after a certain event (e.g., mixture is produced, the material is exposed to air, temperature changes, etc.). Graph 500 shows $\mu 0$, which corresponds to the material's viscosity right when the event occurs at T0. As shown in this example, the viscosity of material A increases from $\mu 0$ to $\mu 1$ during time period T0–T1. Given a time input, the surgical device is able to use the viscosity function and determine a corresponding pressure to achieve a target delivery flow rate. For example, in order to achieve a relatively constant flow rate throughout the delivery, the surgical device may determine a pressure function illustrated in graph 530. Using the pressure function, the surgical device increases the pressure on the plunger during the delivery in order to keep the target flow rate constant, as shown in graph 540. If, however, the pressure is kept constant when delivering material A, the corresponding flow rate decreases exponentially with time. Graph 510 illustrates a constant pressure applied when delivering the material, which results in an exponentially decreasing flow rate shown in graph 520.

As another example, the viscosity may drop as pressure is applied or the material starts to flow (because of shear stress). In this example, the surgical device may decrease the pressure on the plunger during the delivery in order to keep the target flow rate constant. If, in this example, the pressure is kept constant when delivering the material, the corresponding flow rate may increase exponentially with time. Other viscosity behaviors are also contemplated.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for."

What is claimed is:

1. A method of delivering a material to an eye through a syringe, comprising:
   at a controller:
      selecting a material profile corresponding to the material from a plurality of material profiles stored in a memory, each of the plurality of material profiles corresponding to one of a plurality of materials and comprising a stored function of a change in a physical property of the corresponding material over time;
      receiving an indication to initiate a delivery of the material;
      receiving a first indicated time;
      determining a pressure to exert based on the received first indicated time and the selected material profile having the stored function of the material;
      causing the determined pressure to be exerted on a plunger of the syringe to deliver the material to the eye at a target flow rate;
      receiving a second indicated time; and
      causing adjustment to the pressure on the plunger based on the received second indicated time and the stored function to enable a controlled delivery of the material at the target flow rate.

2. The method of claim 1, wherein adjusting the pressure on the plunger comprises:
   at the controller:
      receiving input from a delivery initiation element that indicates the target flow rate at a certain time;
      identifying a corresponding pressure for the target flow rate based on a state of a property of the material at the certain time; and
      causing the corresponding pressure to be applied to achieve the target flow rate.

3. The method of claim 1, wherein the stored function associates a change in a viscosity of the material over time.

4. The method of claim 3, wherein adjusting the pressure comprises adjusting the pressure with time based on the stored function which is a non-linear function corresponding to a change in the viscosity of the material with time.

5. The method of claim 1, wherein adjusting the pressure comprises keeping the target flow rate constant during the controlled delivery of the material to the eye.

6. The method of claim 1, further comprising:
   at the controller:
      causing termination of the exerting of pressure when at least one of a certain time threshold is reached, a viscosity threshold corresponding to a viscosity of the material is reached, or the pressure reaches a certain pressure threshold.

7. The method of claim 1, further comprising:
   at the controller:
      determining when a certain volume of material has been delivered using a realtime analysis based on a delivery time of the material; and
      causing termination of the exerting of pressure when the certain volume of material has been delivered.

8. The method of claim 1, wherein the adjusting is further based on real-time information received from a sensor coupled to the syringe.

9. The method of claim 1, further comprising:
   at the controller:
      causing termination of the controlled delivery; and
      causing reduction of the pressure to a negative pressure.

10. The method of claim 1, wherein adjusting the pressure further comprises adjusting the pressure based on a lag-time between when an event occurs and when the indication to initiate the delivery of the material is received.

* * * * *